(12) United States Patent
Foley et al.

(10) Patent No.: US 10,907,116 B2
(45) Date of Patent: Feb. 2, 2021

(54) OLFACTIVE COMPOSITIONS COMPRISING CYCLOHEXYL-ALKYL CARBINOLS

(71) Applicant: P2 SCIENCE, INC., Woodbridge, CT (US)

(72) Inventors: Patrick Foley, New Haven, CT (US); Yonghua Yang, Niantic, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 395 days.

(21) Appl. No.: 15/578,629

(22) PCT Filed: Jun. 3, 2016

(86) PCT No.: PCT/US2016/035829
§ 371 (c)(1),
(2) Date: Nov. 30, 2017

(87) PCT Pub. No.: WO2016/197000
PCT Pub. Date: Dec. 8, 2016

(65) Prior Publication Data
US 2018/0163158 A1    Jun. 14, 2018

Related U.S. Application Data

(60) Provisional application No. 62/171,063, filed on Jun. 4, 2015.

(51) Int. Cl.
*C11B 9/00* (2006.01)
*C07C 29/143* (2006.01)
(Continued)

(52) U.S. Cl.
CPC .......... *C11B 9/0034* (2013.01); *A23L 27/203* (2016.08); *A61K 8/34* (2013.01);
(Continued)

(58) Field of Classification Search
CPC .... C11B 9/0034; C11B 9/0015; A23L 27/203; C07C 33/14; C07C 29/143; A61K 8/34
See application file for complete search history.

(56) References Cited

U.S. PATENT DOCUMENTS 4,195,099 A * 3/1980 Sprecker .............. A24B 15/403
                                                              426/536
4,283,576 A    8/1981 Sprecker et al.

FOREIGN PATENT DOCUMENTS

EP    1417896 A1    5/2004
EP    2423290 A1    2/2012
(Continued)

OTHER PUBLICATIONS

Angerer, "Synthesis by oxidation of heterosubstituted alkanes", Science of Synthesis, 2004, vol. 26, pp. 39-126.*
(Continued)

*Primary Examiner* — Nikki H. Dees
*Assistant Examiner* — Changqing Li
(74) *Attorney, Agent, or Firm* — Hoxie & Associates LLC

(57) ABSTRACT

The present application relates to the preparation of cyclohexyl-alkyl carbinols, including 1-(cyclohex-3-en-1-yl)-2-methylpropan-1-ol, which possesses a minty aroma that can be described as fresh, invigorating, and menthol-like, and also possesses cooling properties. The use of cyclohexyl-alkyl carbinols as readily accessible and cost effective fragrance, flavor, and cooling ingredients, and potential applications thereof is also described.

12 Claims, 3 Drawing Sheets

$^1$H NMR spectrum of 1-(cyclohex-3-en-1-yl)-2-methylpropan-1-ol

(51) Int. Cl.
    *C07C 33/14*          (2006.01)
    *C07C 69/007*        (2006.01)
    *A61Q 13/00*         (2006.01)
    *C07C 69/24*          (2006.01)
    *A61K 8/34*           (2006.01)
    *A23L 27/20*         (2016.01)
    *C07C 43/162*        (2006.01)
    *C07C 45/69*          (2006.01)
    *C07C 45/72*          (2006.01)
    *C07C 49/543*        (2006.01)

(52) U.S. Cl.
    CPC ............ *A61Q 13/00* (2013.01); *C07C 29/143* (2013.01); *C07C 33/14* (2013.01); *C07C 43/162* (2013.01); *C07C 45/69* (2013.01); *C07C 45/72* (2013.01); *C07C 49/543* (2013.01); *C07C 69/007* (2013.01); *C07C 69/24* (2013.01); *C07C 2601/16* (2017.05)

(56) References Cited

FOREIGN PATENT DOCUMENTS

| | | | |
|---|---|---|---|
| FR | 1294932 A | 6/1962 | |
| GB | 1476720 A | 6/1977 | |
| JP | 59001462 A | 4/1984 | |
| WO | WO-2013109798 A2 * | 7/2013 | ........... A61K 8/4973 |

OTHER PUBLICATIONS

English Abstract of JP 59001462 A, published on Jun. 1, 1984, 1 page.

* cited by examiner

¹H NMR spectrum of 1-(cyclohex-3-en-1-yl)-2-methylpropan-1-ol $^{13}$C NMR spectrum of 1-(cyclohex-3-en-1-yl)-2-methylpropan-1-ol Gas Chromatogram with Flame Ionization Detector of 1-(cyclohex-3-en-1-yl)-2-methylpropan-1-ol

OLFACTIVE COMPOSITIONS COMPRISING CYCLOHEXYL-ALKYL CARBINOLS

CROSS-REFERENCE TO RELATED APPLICATIONS

This application is a U.S. National Stage application of International Application No. PCT/US2016/035829 filed on Jun. 3, 2016, which claims the benefit of and priority to U.S. Provisional Patent Application No. 62/171,063, filed Jun. 4, 2015, the entirety of which is incorporated by reference herein.

BACKGROUND

Scent is an important factor to produce a sense of anticipation, quality, palatability, and security to the effect of products. Identifying effective aroma products and characteristics is powerful in attracting additional customers. Sweet, resinous smells are particularly desirable in many formulations including those for use in toiletry products, cosmetics, household cleaners, air care, laundry, and fine fragrance applications.

Physiological cooling agents, commonly known as coolants, continue to gain popularity for use in various consumer applications due to their recognized ability for improving desirable sensate properties in consumer products. The desired sensate properties are generally explained by the chemical action of such coolant compounds on the nerve endings responsible for the sensation of cold. Common applications and uses for these compounds include, but are not limited to foods, beverages, flavors, pharmaceuticals, perfumes, and miscellaneous cosmetic goods.

SUMMARY 1-(cyclohex-3-en-1-yl)-2-methylpropan-1-ol, compound (I), possesses a minty aroma, which can be described as fresh, invigorating, and menthol-like.

Scheme 1. 1-(cyclohex-3-en-1-yl)-2-methylpropan-1-ol, compound (I).

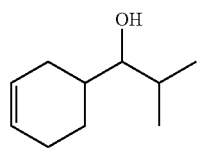

(I)

1-(cyclohex-3-en-1-yl)-2-methylpropan-1-ol has never been described and characterized as a flavor or fragrance ingredient, nor as a coolant. This application describes the preparation of 1-(cyclohex-3-en-1-yl)-2-methylpropan-1-ol, its surprising and unexpected olfactive qualities, its use as a readily accessible and cost effective fragrance ingredient, flavor ingredient, and coolant, and potential applications thereof. The preparation of diastereomerically and/or enantiomerically enriched compositions of 1-(cyclohex-3-en-1-yl)-2-methylpropan-1-ol is also described. Further, the application describes the preparation of other cyclohexyl-alkyl carbinols, e.g., compounds of formulas (6), (I'), and (I"), and their use as a readily accessible and cost effective fragrance ingredient, flavor ingredient, and coolant, and potential applications thereof.

In one aspect, the application relates to a fragrance composition comprising 1-(cyclohex-3-en-1-yl)-2-methylpropan-1-ol, compound (I).

In another aspect, the application relates to a fragrance composition comprising 1-(cyclohex-3-en-1-yl)-2-methylpropan-1-ol, compound (I), and one or more additives.

In another aspect, the application relates to a flavor composition comprising 1-(cyclohex-3-en-1-yl)-2-methylpropan-1-ol, compound (I).

In another aspect, the application relates to a flavor composition comprising 1-(cyclohex-3-en-1-yl)-2-methylpropan-1-ol, compound (I), and one or more additives.

In one aspect, the application relates to a physiologically cooling composition comprising 1-(cyclohex-3-en-1-yl)-2-methylpropan-1-ol, compound (I).

In another aspect, the application relates to a physiologically cooling composition comprising 1-(cyclohex-3-en-1-yl)-2-methylpropan-1-ol, compound (I), and one or more additives.

In another aspect, the application relates to a composition comprising each of the four stereoisomers of 1-(cyclohex-3-en-1-yl)-2-methylpropan-1-ol, compound (I), wherein the composition comprises a non-statistical mixture of stereoisomers Ia, Ib, Ic, and Id, i.e., not a 1:1:1:1 mixture.

Scheme 2. Stereoisomers of 1-(cyclohex-3-en-1-yl)-2-methylpropan-1-ol (I).

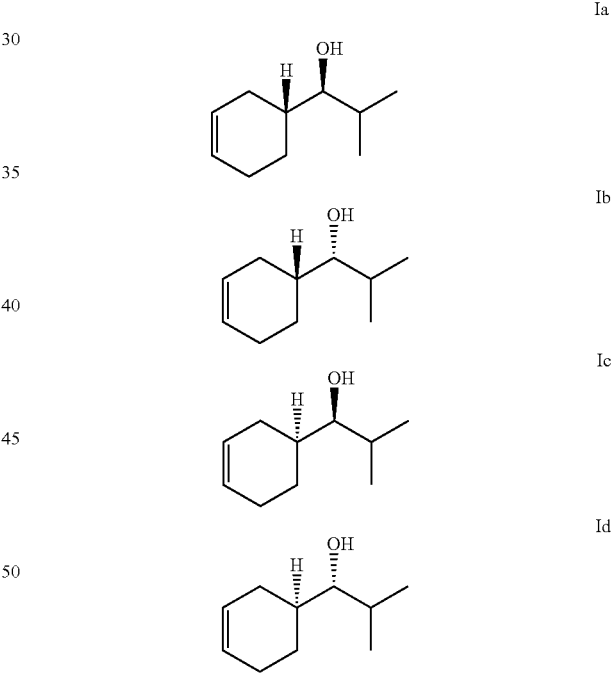

In one aspect, the application relates to a fragrance composition comprising a non-statistical mixture of stereoisomers Ia, Ib, Ic, and Id.

In another aspect, the application relates to a fragrance composition comprising a non-statistical mixture of stereoisomers Ia, Ib, Ic, and Id, and one or more additives.

In another aspect, the application relates to a flavor composition comprising a non-statistical mixture of stereoisomers Ia, Ib, Ic, and Id.

In another aspect, the application relates to a flavor composition comprising a non-statistical mixture of stereoisomers Ia, Ib, Ic, and Id, and one or more additives.

In one aspect, the application relates to a physiologically cooling composition comprising a non-statistical mixture of stereoisomers Ia, Ib, Ic, and Id.

In one aspect, the application relates to a physiologically cooling composition comprising a non-statistical mixture of stereoisomers Ia, Ib, Ic, and Id, and one or more additives.

In one aspect, the application relates to fragrance compositions, flavor compositions, and physiologically cooling compositions comprising a compound of the application, and, optionally, one or more additives.

In a further aspect, the application relates to fragrance compositions, flavor compositions, and physiologically cooling compositions comprising a compound of formula (6), (I'), or (I"), and, optionally, one or more additives.

In another aspect, compounds of the application have pheromone-like properties. In a further aspect, compounds of the application may have utility in the preparation of compositions for use in controlling insect and pest populations.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. In addition, the materials, methods, and examples are illustrative only and are not intended to be limiting.

Other features and advantages of the application will be apparent from the following detailed description and claims.

DETAILED DESCRIPTION OF THE APPLICATION

Figure 1:
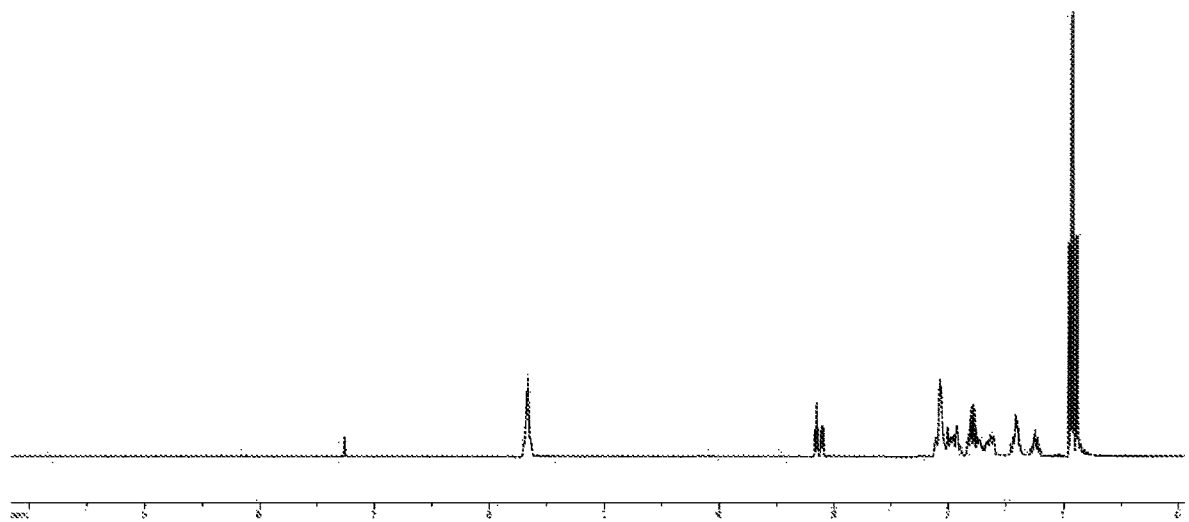
FIG. 1 is a $^1$H NMR spectrum of 1-(cyclohex-3-en-1-yl)-2-methylpropan-1-ol.
Figure 2:
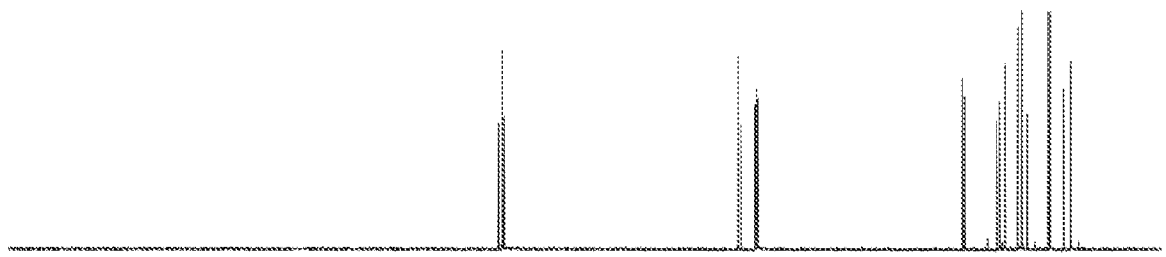
FIG. 2 is a $^{13}$C NMR spectrum of 1-(cyclohex-3-en-1-yl)-2-methylpropan-1-ol.
Figure 3:
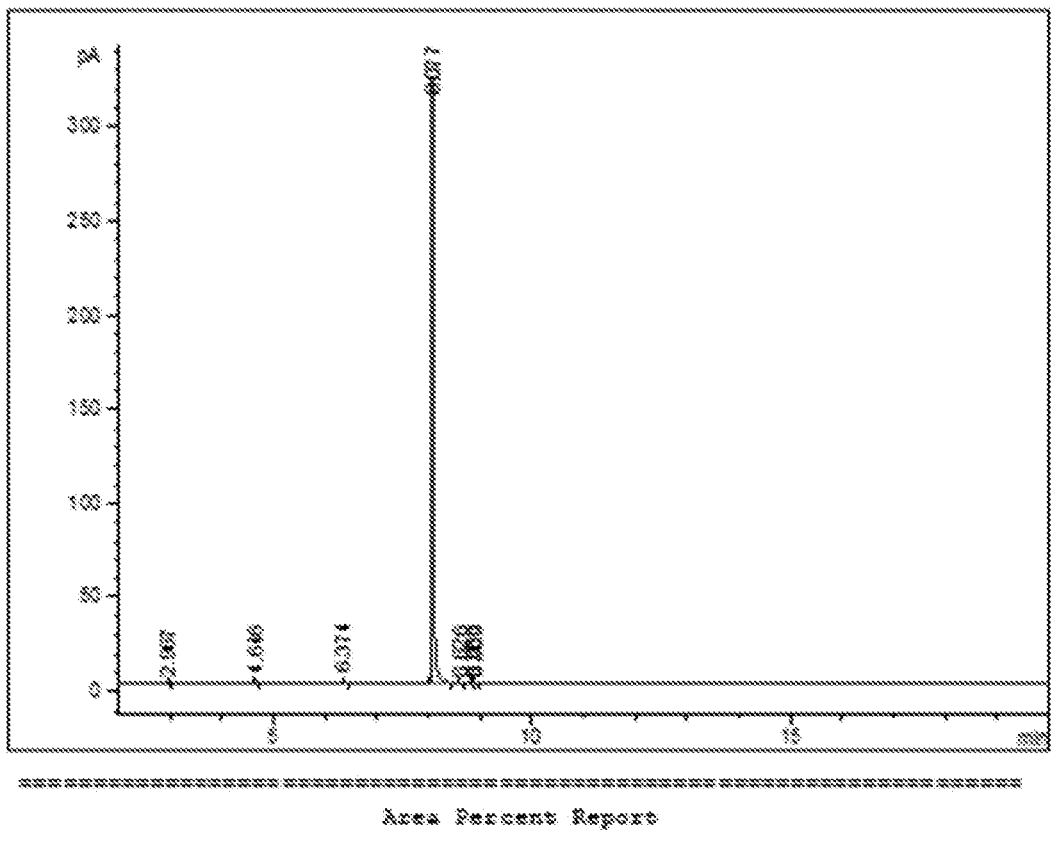
FIG. 3 is a Gas Chromatogram with Flame Ionization Detector of 1-(cyclohex-3-en-1-yl)-2-methylpropan-1-ol.

The application is directed to compound (I), compounds of formula (6), compounds of formula (I'), and compounds of formula (I"), all of which are referred to collectively herein as "the compounds" or "the compounds of the present application", as compounds having desirable flavor, fragrance, and cooling properties such that it may be considered for use as a novel flavor, fragrance, and cooling ingredient. For clarity, the compounds of the application are referred to by their chemical name or by "a compound of the application", "the compound of the application" or "the compounds of the application" to differentiate it from known fragrance, flavor, and cooling ingredients used in flavor, fragrance, and cooling compositions.

1-(cyclohex-3-en-1-yl)-2-methylpropan-1-ol, i.e., compound (I), possesses a fresh, minty, menthol-like smell. Compound (I) has been determined to be useful for numerous fragrance and flavor compositions and for physiologically cooling compositions. As such, the application is applicable wherever the inclusion of a pleasing fragrance, flavor, or cooling effect is desired.

In one aspect, the application relates to a fragrance composition comprising compound (I),

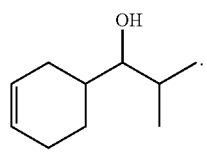

In one aspect, the application relates to a fragrance composition comprising compound (I) and one or more additives.

In another aspect, the application relates to a flavor composition comprising compound (I).

In one aspect, the application relates to a flavor composition comprising compound (I) and one or more additives.

In another aspect, the application relates to a physiologically cooling composition comprising compound (I).

In one aspect, the application relates to a physiologically cooling composition comprising compound (I) and one or more additives.

There are four stereoisomers of compound (I):

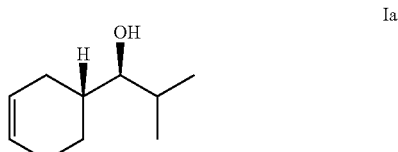

Ia

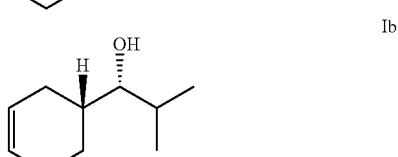

Ib

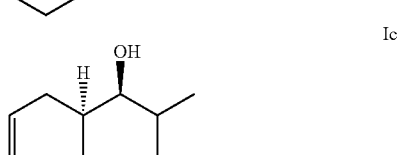

Ic

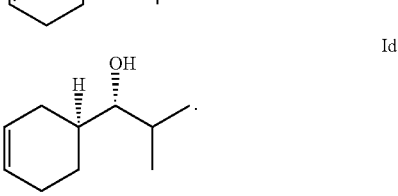

Id

In one aspect, the application relates to compound (I), wherein compound (I) is enantio- and/or diastereoenriched, i.e., there is a non-statistical mixture, i.e., not a 1:1:1:1 mixture, of each of the four stereoisomers: Ia, Ib, Ic, and Id.

In one aspect, the application relates to a fragrance composition, a flavor composition, and a physiologically cooling composition of compound (I), comprising stereoisomers Ia, Ib, Ic, and Id, and, optionally one or more additives, wherein stereoisomer Ia is present in compound (I) in an amount greater than 25%; In a further aspect, stereoisomer Ia is present in compound (I) in an amount greater than about 30%; In a further aspect, stereoisomer Ia is present in compound (I) in an amount greater than about 35%; In a further aspect, stereoisomer Ia is present in compound (I) in an amount greater than about 40%; In a further aspect, stereoisomer Ia is present in compound (I) in an amount greater than about 50%; In a further aspect, stereoisomer Ia is present in compound (I) in an amount greater than about 55%: In a further aspect, stereoisomer Ia is present in compound (I) in an amount greater than about 60%; In a further aspect, stereoisomer Ia is present in compound (I) in an amount greater than about 65%; In a further aspect, stereoisomer Ia is present in compound (I) in an amount greater than about 70%; In a further aspect, stereoisomer Ia is present in compound (I) in an amount greater than about 75%; In a further aspect, stereoisomer Ia is present in compound (I) in an amount greater than about 80%; In a further aspect, stereoisomer Ia is present in compound (I) in an amount greater than about 85%; In a further aspect, stereoisomer Ia is present in compound (I) in an amount greater than about 90%; In a further aspect, stereoisomer Ia is present in compound (I) in an amount greater than about 95%; In a further aspect, stereoisomer Ia is present in compound (I) in an amount greater than about 96%; In a further aspect, stereoisomer Ia is present in compound (I) in an amount greater than about 97%; In a further aspect, stereoisomer Ia is present in compound (I) in an amount greater than about 98%; In a further aspect, stereoisomer Ia is present in compound (I) in an amount and greater than about 99%.

In one aspect, the application relates to a fragrance composition, a flavor composition, and a physiologically cooling composition of compound (I), comprising stereoisomers Ia, Ib, Ic, and Id, and, optionally one or more additives, wherein stereoisomer Ib is present in compound (I) in an amount greater than about 25%; In a further aspect, stereoisomer Ib is present in compound (I) in an amount greater than about 30%; In a further aspect, stereoisomer Ib is present in compound (I) in an amount greater than about 35%; In a further aspect, stereoisomer Ib is present in compound (I) in an amount greater than about 40%; In a further aspect, stereoisomer Ib is present in compound (I) in an amount greater than about 50%; In a further aspect, stereoisomer Ib is present in compound (I) in an amount greater than about 55%: In a further aspect, stereoisomer Ib is present in compound (I) in an amount greater than about 60%; In a further aspect, stereoisomer Ib is present in compound (I) in an amount greater than about 65%; In a further aspect, stereoisomer Ib is present in compound (I) in an amount greater than about 70%; In a further aspect, stereoisomer Ib is present in compound (I) in an amount greater than about 75%; In a further aspect, stereoisomer Ib is present in compound (I) in an amount greater than about 80%; In a further aspect, stereoisomer Ib is present in compound (I) in an amount greater than about 85%; In a further aspect, stereoisomer Ib is present in compound (I) in an amount greater than about 90%; In a further aspect, stereoisomer Ib is present in compound (I) in an amount greater than about 95%; In a further aspect, stereoisomer Ib is present in compound (I) in an amount greater than about 96%; In a further aspect, stereoisomer Ib is present in compound (I) in an amount greater than about 97%; In a further aspect, stereoisomer Ib is present in compound (I) in an amount greater than about 98%; In a further aspect, stereoisomer Ib is present in compound (I) in an amount and greater than about 99%.

In one aspect, the application relates to a fragrance composition, a flavor composition, and a physiologically cooling composition of compound (I), comprising stereoisomers Ia, Ib, Ic, and Id, and, optionally one or more additives, wherein stereoisomer Ic is present in compound (I) in an amount greater than about 25%; In a further aspect, stereoisomer Ic is present in compound (I) in an amount greater than about 30%; In a further aspect, stereoisomer Ic is present in compound (I) in an amount greater than about 35%; In a further aspect, stereoisomer Ic is present in compound (I) in an amount greater than about 40%; In a further aspect, stereoisomer Ic is present in compound (I) in an amount greater than about 50%; In a further aspect, stereoisomer Ic is present in compound (I) in an amount greater than about 55%: In a further aspect, stereoisomer Ic is present in compound (I) in an amount greater than about 60%; In a further aspect, stereoisomer Ic is present in compound (I) in an amount greater than about 65%; In a further aspect, stereoisomer Ic is present in compound (I) in an amount greater than about 70%; In a further aspect, stereoisomer Ic is present in compound (I) in an amount greater than about 75%; In a further aspect, stereoisomer Ic is present in compound (I) in an amount greater than about 80%; In a further aspect, stereoisomer Ic is present in compound (I) in an amount greater than about 85%; In a further aspect, stereoisomer Ic is present in compound (I) in an amount greater than about 90%; In a further aspect, stereoisomer Ic is present in compound (I) in an amount greater than about 95%; In a further aspect, stereoisomer Ic is present in compound (I) in an amount greater than about 96%; In a further aspect, stereoisomer Ic is present in compound (I) in an amount greater than about 97%; In a further aspect, stereoisomer Ic is present in compound (I) in an amount greater than about 98%; In a further aspect, stereoisomer Ic is present in compound (I) in an amount and greater than about 99%.

In one aspect, the application relates to a fragrance composition, a flavor composition, and a physiologically cooling composition of compound (I), comprising stereoisomers Ia, Ib, Ic, and Id, and, optionally one or more additives, wherein stereoisomer Id is present in compound (I) in an amount greater than about 25%; In a further aspect, stereoisomer Id is present in compound (I) in an amount greater than about 30%; In a further aspect, stereoisomer Id is present in compound (I) in an amount greater than about 35%; In a further aspect, stereoisomer Id is present in compound (I) in an amount greater than about 40%; In a further aspect, stereoisomer Id is present in compound (I) in an amount greater than about 50%; In a further aspect, stereoisomer Id is present in compound (I) in an amount greater than about 55%: In a further aspect, stereoisomer Id is present in compound (I) in an amount greater than about 60%; In a further aspect, stereoisomer Id is present in compound (I) in an amount greater than about 65%; In a further aspect, stereoisomer Id is present in compound (I) in an amount greater than about 70%; In a further aspect, stereoisomer Id is present in compound (I) in an amount greater than about 75%; In a further aspect, stereoisomer Id is present in compound (I) in an amount greater than about 80%; In a further aspect, stereoisomer Id is present in compound (I) in an amount greater than about 85%; In a further aspect, stereoisomer Id is present in compound (I) in an amount greater than about 90%; In a further aspect, stereoisomer Id is present in compound (I) in an amount greater than about 95%; In a further aspect, stereoisomer Id is present in compound (I) in an amount greater than about 96%; In a further aspect, stereoisomer Id is present in compound (I) in an amount greater than about 97%; In a further aspect, stereoisomer Id is present in compound (I) in an amount greater than about 98%; In a further aspect, stereoisomer Id is present in compound (I) in an amount and greater than about 99%.

In one aspect, the application relates to fragrance compositions, flavor compositions, and physiologically cooling compositions comprising a compound of the application, and, optionally, one or more additives.

In a further aspect, the application relates to fragrance compositions, flavor compositions, and physiologically cooling compositions comprising a compound of formula (6), (I'), or (I''), and, optionally, one or more additives.

In one aspect, the compounds of the application exhibit pheromone-like properties. See Guiotto, A. et al. *Farmaco, Edizione Scientifica* 1980, 35(6), 441-446. In a further aspect, compounds of the application may have utility in the preparation of compositions for use in controlling insect and pest populations.

In one aspect, compositions for the use in controlling insect and pest populations comprise one or more compounds of the application and at least one additive, solvent, and/or carrier. In one aspect, the solvent is a mixture of distilled water, iso-propanol, and/or witch hazel. In one aspect, the additive comprises one or more dried herbs. In one aspect the additive is mint.

In one aspect, compositions for the use in controlling insect and pest populations comprise one or more compounds of the application and a solubilizer, a propellant, and a fragrance additive. Non-limiting examples of solubilizers include: water, ethanol, iso-propanol, n-propanol, n-butanol, and s-butanol. Non-limiting examples of propellants include: propane, butane, iso-butane, dimethyl ether, methyl ethyl ether, nitrous oxide, carbon dioxide, hydrofluoroalkanes (e.g., 1,1,1,2-tetrafluoroethane, 1,1,1,2,3,3,3-heptafluoropropane), and combinations thereof.

In one aspect, the compounds of the application may be prepared by reacting aldehydes with Grignard reagents to afford the desired carbinol. For example, compound (I) may be prepared by reaction of aldehyde (1) with iso-propyl magnesium chloride.

Scheme 3. Grignard synthesis of 1-(cyclohex-3-en-1-yl)-2-methylpropan-1-ol.

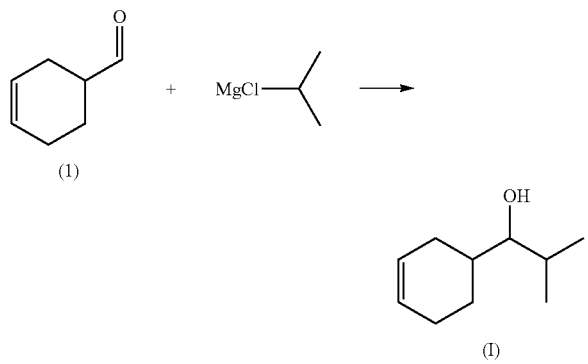

In one aspect, compound (I) of the application may be prepared according to a process comprising the steps of: (1) aldol condensation reaction of formaldehyde (A) with 3-methyl-2-butanone (B) to provide 4-methyl-pent-1-en-3-one (C); (2) Diels-Alder reaction of (C) with 1,3-butadiene (D) to provide cyclohexenone (E); and (3) reduction of cyclohexenone (E) to provide compound (I).

Scheme 4. Three-Step Synthesis of Compound (I).

Step 1
Aldol Condensation

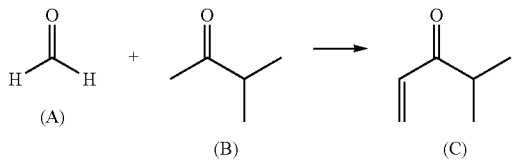

Step 2
Asymmetric Diels-Alder

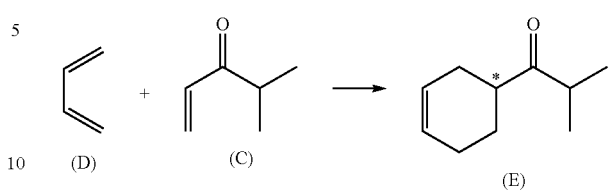

Step 3
Asymmetric Reduction

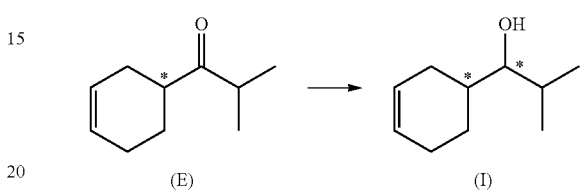

In one aspect of the application, one or both of steps 2 and 3 in Scheme 4 may be conducted to achieve enantioselectivity and/or diastereoselectivity in the product mixture.

In one aspect, the Diels-Alder reaction of (D) and (C) may be conducted using a chiral catalyst to provide cyclohexenone (E) enantioselectively. See Hayashi, Y. et al. *Angew. Chem. Int. Ed.* 2008, 47, 6634-6637.

In one aspect, cyclohexenone (E) may be prepared with enantiomeric excesses (ee's) greater than 50%. In a further aspect, cyclohexenone (E) may be prepared with greater than 60% ee; In a further aspect, cyclohexenone (E) may be prepared with greater than 70% ee; In a further aspect, cyclohexenone (E) may be prepared with greater than 80% ee; In a further aspect, cyclohexenone (E) may be prepared with greater than 90% ee; In a further aspect, cyclohexenone (E) may be prepared with greater than 95% ee; In a further aspect, cyclohexenone (E) may be prepared with greater than 98% ee; In a further aspect, cyclohexenone (E) may be prepared with greater than 99% ee.

In one aspect, the reduction of enantiomerically enriched cyclohexenone (E) may be conducted using a chiral catalyst to provide compound (I) in diastereomerically and enantiomerically enriched forms. See Okuma, T. et al. *J. Am. Chem. Soc.* 1995, 117, 10417-10418.

In one aspect, compounds of the application may be prepared according to the strategy in Scheme 5.

Scheme 5. Synthesis of Cyclohexyl-Alkyl Ketones (6), Cyclohexyl-Alkyl carbinols (I'), and Esters and Ethers Thereof (I").

Step (a):

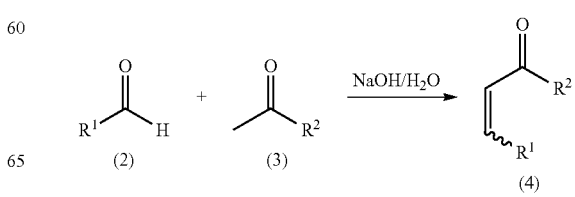

-continued

Step (b):

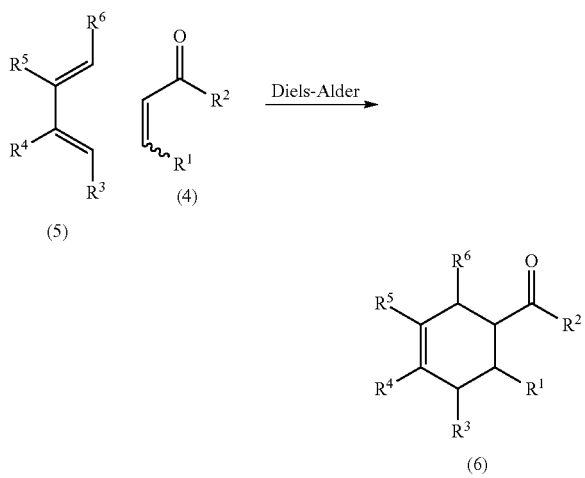

Step (c):

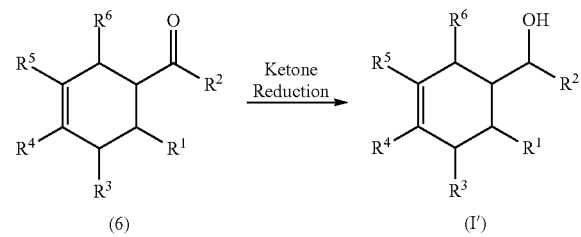

Step (d):

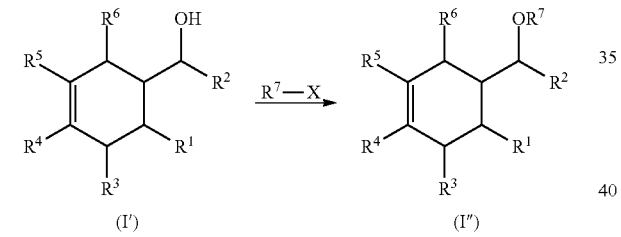

In one aspect, compounds of the application may be prepared according to a process comprising: (a) aldol condensation reaction of an aldehyde of formula (2) with a ketone of formula (3) providing alkenones of formula (4); (b) Diels-Alder reaction of a diene of formula (5) with an alkenone of formula (4) providing a cyclohexenone of formula (6); (c) reduction of cyclohexenone of formula (6) providing a cyclohexyl-alkyl-carbinol (I'); and, optionally, (d) reacting cyclohexyl-alkyl-carbinol (I') with an electrophile, $R^7$—X, providing an ester or ether compound (I''); wherein:
$R^1$ is H, $C_1$-$C_6$ alkyl, C(O)OH, C(O)O—$C_1$-$C_6$ alkyl, or O—($C_1$-$C_6$ alkyl)-OH;
$R^2$ is $C_1$-$C_6$ alkyl or $C_3$-$C_6$ cycloalkyl;
$R^3$, $R^4$, $R^5$, and $R^6$ are each independently H, methyl, C(O)OCH$_3$, C(O)OCH$_2$CH$_3$, methoxy, ethoxy, or trimethylsiloxy; and
$R^7$ is $C_1$-$C_6$ alkyl, C(O)—$C_1$-$C_6$ alkyl, ($C_1$-$C_6$ alkyl)-OH, or ($C_1$-$C_6$ alkyl)-O—($C_1$-$C_6$ alkyl).

In one aspect of the application, one or both of steps (b) and (c) in Scheme 5 may be conducted to achieve enantioselectivity and/or diastereoselectivity in the product mixture.

In one aspect, the Diels-Alder reaction in step (b) of (5) and (4) may be conducted using a chiral catalyst to provide cyclohexenone (6) enantioselectively. See Hayashi, Y. et al. *Angew. Chem. Int. Ed.* 2008, 47, 6634-6637.

In one aspect, cyclohexenone (6) may be prepared with enantiomeric excesses (ee's) greater than 50%. In a further aspect, cyclohexenone (6) may be prepared with greater than 60% ee; In a further aspect, cyclohexenone (6) may be prepared with greater than 70% ee; In a further aspect, cyclohexenone (6) may be prepared with greater than 80% ee; In a further aspect, cyclohexenone (6) may be prepared with greater than 90% ee; In a further aspect, cyclohexenone (6) may be prepared with greater than 95% ee; In a further aspect, cyclohexenone (6) may be prepared with greater than 98% ee; In a further aspect, cyclohexenone (6) may be prepared with greater than 99% ee.

In one aspect, the reduction in step (c) of enantiomerically enriched cyclohexenone (6) may be conducted using a chiral catalyst to provide compound (I') in diastereomerically and enantiomerically enriched forms. See Okuma, T. et al. *J. Am. Chem. Soc.* 1995, 117, 10417-10418.

In a further aspect, a cyclohexyl-alkyl-carbinol of formula (I') can be reacted with lactic acid to prepare a cyclohexyl-alkyl lactate ester.

In a further aspect, a cyclohexyl-alkyl-carbinol of formula (I') can be reacted with a $C_4$-$C_6$ dicarboxylic acid to prepare a cyclohexyl-alkyl-mono ester and/or a cyclohexyl-alkyl-di-ester.

In a further aspect, a cyclohexyl-alkyl-carbinol (I') can be reacted with appropriately protected electrophiles to prepare, after deprotection, cyclohexyl-alkyl ethylene glycol ethers, propylene glycol ethers and glycerol ethers.

Scheme 6. Glycol and Glycerol Ether Variants of Cyclohexyl-Alkyl Carbinols (I')

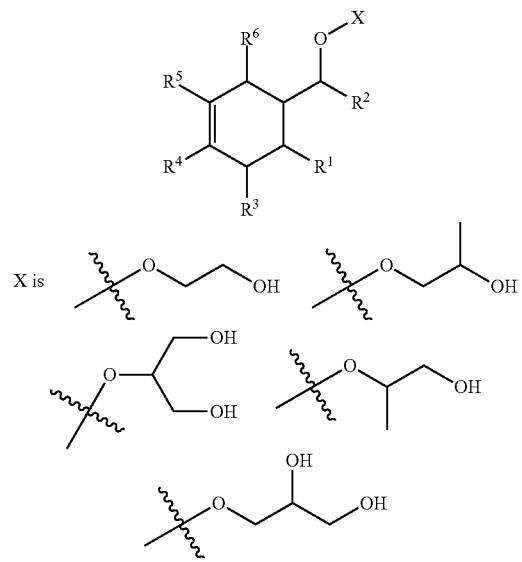

In a further aspect, a cyclohexyl-alkyl-carbinol of formula (I') can be reacted with isocyanates to prepare cyclohexyl-alkyl-carbamates.

In one aspect, when $R^1$, $R^3$, $R^4$, $R^5$, and $R^6$ are each H and $R^2$ is tert-butyl, the cyclohexyl-alkyl carbinol product of Formula (I') is a reduced form of a naturally occurring ketone isolated from the essential oil of Korean *Perilla* leaves. See *Asian Journal of Chemistry* 2012, 24(7), 3221-3224.

Scheme 7. Access to a naturally occurring ketone and its corresponding cyclohexyl-alkyl carbinol.

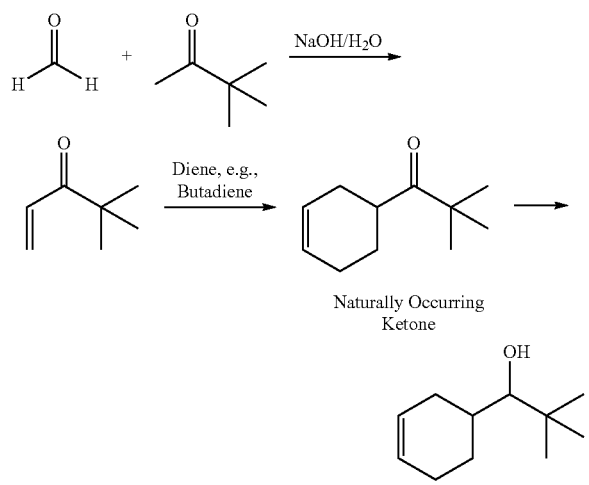

Naturally Occurring Ketone

In another aspect, compounds of the application may be prepared according to the strategy in Scheme 8.

Scheme 8. Synthesis of Bridged Ring System Compounds.

Step (a):

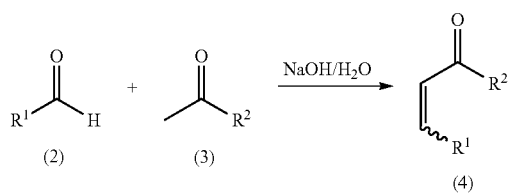

Step (b):

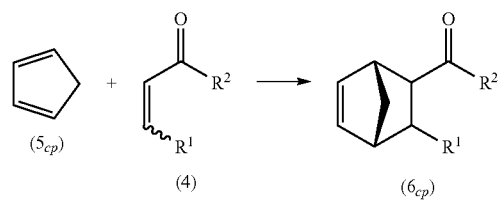

Step (c):

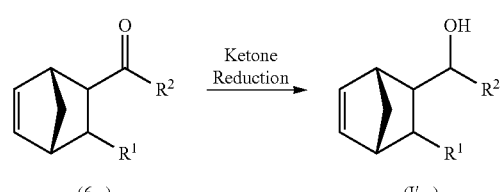

Step (d):

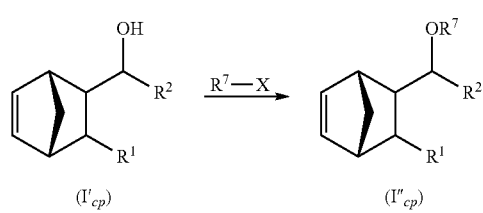

In one aspect, compounds of the application can be prepared according to a process comprising (a) aldol condensation reaction of an aldehyde of formula (2) with a ketone of formula (3) providing an alkenone of formula (4); (b) Diels-Alder reaction of cyclopentadiene ($5_{cp}$) with an alkenone of formula (4) providing a cyclohexenone of formula ($6_{cp}$); (c) reduction of cyclohexenone of formula ($6_{cp}$) providing a carbinol ($I'_{cp}$); and, optionally, (d) reacting carbinol ($I'_{cp}$) with an electrophile, $R^7$—X, providing an ester or ether compound ($I''_{cp}$); wherein:

$R^1$ is H, $C_1$-$C_6$ alkyl, C(O)OH, C(O)O—$C_1$-$C_6$ alkyl, or O—($C_1$-$C_6$ alkyl)-OH;

$R^2$ is $C_1$-$C_6$ alkyl or $C_3$-$C_6$ cycloalkyl; and $R^7$ is $C_1$-$C_6$ alkyl, C(O)—$C_1$-$C_6$ alkyl, ($C_1$-$C_6$ alkyl)-OH, or ($C_1$-$C_6$ alkyl)-O—($C_1$-$C_6$ alkyl).

In one aspect, compounds of the application can be prepared according to a prepared according to the strategy in Scheme 9.

Scheme 9. Synthesis of Hydroxymethyl Compounds of the Application.

Step (a):

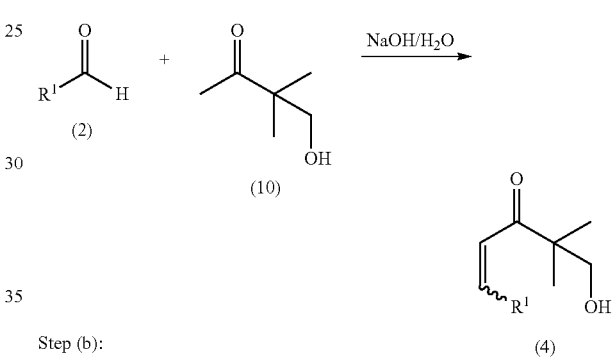

Step (b):

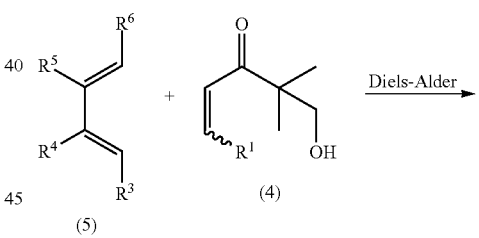

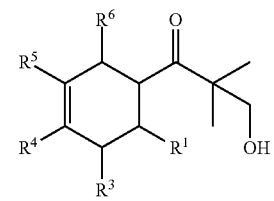

Step (c):

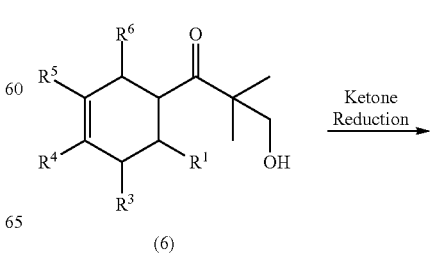

-continued

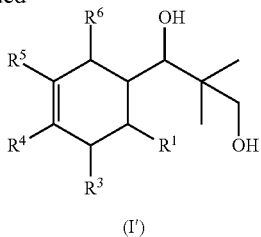

(I')

In one aspect, compounds of the application may be prepared according to a process comprising: (a) aldol condensation reaction of an aldehyde of formula (2) with hydroxypinacolone (10) providing an alkenone of formula (4); (b) Diels-Alder reaction of a diene of formula (5) with an alkenone of formula (4) providing a cyclohexenone of formula (6); and (c) reduction of a cyclohexenone of formula (6) providing a cyclohexyl-alkyl-carbinol (I'); wherein: $R^1$ is H, $C_1$-$C_6$ alkyl, C(O)OH, C(O)O—$C_1$-$C_6$ alkyl, or O—($C_1$-$C_6$ alkyl)-OH; and
$R^3$, $R^4$, $R^5$, and $R^6$ are each independently H, methyl, C(O)OCH$_3$, C(O)OCH$_2$CH$_3$, methoxy, ethoxy, or trimethylsiloxy.

In a further aspect, compounds of Formula (6) in Scheme 9 can be functionalized to the ketal and further reduced to a glycol or glycerol ether as described in the art. See Tetrahedron Lett. 2011, 1281-1283.

In one aspect, the application relates to a novel synthetic preparation and entry into known coolant compounds (Scheme 10). The ethoxy ether derivative of menthol (13) may be prepared using a two-step synthesis: first, ketalization of menthone (11) with ethylene glycol to provide menthone ketal (12); followed by reduction of (12) to provide compound (13).

Scheme 10. Two-Step Synthesis of Ethoxy Ether Derivative of Menthol.

In another aspect, various ketals can be similarly reduced. The primary alcohol in the ethoxy ether derivative of menthol (13) can be further functionalized into an ester, ether, carbamate, or carboxamide. Menthol carboxamide compounds are reported to be useful cooling agents. See U.S. 2005/0265930.

As used herein, the term "fragrance composition" means a mixture of fragrance ingredients, including auxiliary substances and additives if desired, dissolved in a suitable solvent or mixed with a powdery substrate used to provide a desired odor to a product. Examples of products having fragrance compositions include, but are not limited to, perfumes, soaps, air fresheners, laundry detergent, household cleaning products, liquid or bar soap, shampoo, conditioner, hairspray, cosmetic, makeup, deodorant, insect repellant, insecticide, or pet litter.

In one embodiment, the fragrance composition is for use in a perfume, parfum, extrait, Esprit de Parfum, Parfum de Toilette, Eau de Toilette, or Eau de Cologne.

In one embodiment, the fragrance composition is for use in an air freshner, e.g., a spray, candle, oil, bead, wax melt, plug-in, fabric refresher, or car air freshner.

In one embodiment, the fragrance composition is for use in a household or industrial cleaning product. In one embodiment, the household cleaner is bleach, a shower/bath cleaning product, a toilet cleaning product, a glass cleaning product, a tile cleaning product, a wood cleaning product, a carpet-cleaning product, or a granite cleaning product. In one embodiment, the industrial cleaner is an all-purpose cleaner, a high-performance cleaner, or a degreaser.

In one embodiment, the fragrance composition is for use in a cosmetic, make up, or make up products.

In one embodiment, the fragrance composition is for use in health and personal care products, e.g., after shave, deodorant, medical spray (athlete's foot), sunscreen, sunburn treatment, wrinkle creams, exfoliator, scrub, moisturizer, lotion, powder, hand soap, hand santizer, bar soap, liquid soap, body wash, shampoo, conditioner, baby shampoo, baby oil, acne bar soap, acne cream, and acne gel.

In one embodiment, the fragrance composition is for use in pet litter.

As used herein, the term "flavor composition" means a mixture of flavor ingredients, including auxiliary substances and additives if desired, dissolved in a suitable solvent or mixed with a powdery substrate used to provide a desired flavor to a product. Examples of products having flavor compositions include, but are not limited to, dental hygiene products such as mouth wash, toothpaste, floss, and breath fresheners, orally administered medications including liquids, tablets or capsules, and food products.

As used herein, the term "physiological cooling composition" or "cooling composition" means a mixture of ingredients, including auxiliary substances and additives if desired, optionally dissolved in a suitable solvent, used to provide a cooling effect. The cooling compositions of the present application can be used in any consumer good capable of using a cooling agent. In one aspect, the liquid compositions according to the application are suitable for human consumption. In another aspect, the consumer goods are suitable for topical application to mammalian skin, including without limitation, human as well as veterinary applications. More specific examples of consumer goods include, without limitation, flavor blends, foods, cosmetic preparations, confectionery, soft and alcoholic beverages, chewing gums, toothpaste, dental floss, mouthwash, anti-plaque compositions, anti-gingivitis compositions, shampoos, antidandruff shampoos, lotions, deodorants, after shave lotions, shaving gels, shaving aid composites, fragrances, skin sanitizing compositions, throat lozenges, throat drops, chewable antacid tablets, or pharmaceutical compositions or medications, including anti-inflammatory compositions, compositions for treatment of nasal symptoms, for upper gastrointestinal tract distress, for treating cold symptoms, for cough relief, for alleviating discomfort of hot flash, or for foot therapy, and the like.

Fragrance ingredients, flavor ingredients, cooling ingredient, and mixtures thereof that may be used in combination with the disclosed compounds for the manufacture of fragrance, flavor, and cooling compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furans, ketals, nitriles, acids, and hydrocarbons, including both saturated and unsaturated compounds and aliphatic carbocyclic and heterocyclic compounds, and animal products.

Fragrance, flavor, and cooling compositions containing compounds of the application may also contain one or more additives selected from the group consisting of, e.g., esters, alcohols, carboxamides, aldehydes, ketones, acetals, phenols, ethers, lactones, furans, hydrocarbons, and acids.

Examples of esters which may be used in fragrance, flavor, and cooling compositions of the present application include, but are not limited to, acrylic acid esters (methyl, ethyl, etc.), acetoacetic acid esters (methyl, ethyl, etc.), anisic acid esters (methyl, ethyl, etc.), benzoic acid esters (allyl, isoamyl, ethyl, geranyl, linalyl, phenylethyl, hexyl, cis-3-hexenyl, benzyl, methyl, etc.), anthranilic acid esters (cinnamyl, cis-3-hexenyl, methyl, ethyl, linalyl, isobutyl, etc.), N-methylanthranilic acid esters (methyl, ethyl, etc.), isovaleric acid esters (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), isobutyric acid esters (isoamyl, geranyl, citronellyl, terpenyl, cinnamyl, octyl, nellyl, phenylethyl, phenylpropyl, phenoxyethyl, butyl, propyl, isopropyl, hexyl, benzyl, methyl, ethyl, linalyl, rhodinyl, etc.), undecylenic acid esters (allyl, isoamyl, butyl, ethyl, methyl, etc.), octanoic acid esters (allyl, isoamyl, ethyl, octyl, hexyl, butyl, methyl, linalyl, etc.), octenoic acid esters (methyl, ethyl, etc.), octynecarboxylic acid esters (methyl, ethyl, etc.), caproic acid esters (allyl, amyl, isoamyl, methyl, ethyl, isobutyl, propyl, hexyl, cis-3-hexenyl, trans-2-hexenyl, linalyl, geranyl, cyclohexyl, etc.), hexenoic acid esters (methyl, ethyl, etc.), valeric acid esters (amyl, isopropyl, isobutyl, ethyl, cis-3-hexenyl, trans-2-hexenyl, cinnamyl, phenylethyl, methyl, etc.), formic acid esters (anisyl, isoamyl, isopropyl, ethyl, octyl, geranyl, citronellyl, cinnamyl, cyclohexyl, terpenyl, phenylethyl, butyl, propyl, hexyl, cis-3-hexenyl, benzyl, linalyl, rhodinyl, etc.), crotonic acid esters (isobutyl, ethyl, cyclohexyl, etc.), cinnamic acid esters (allyl, ethyl, methyl, isopropyl, propyl, 3-phenylpropyl, benzyl, cyclohexyl, methyl, etc.), succinic acid esters (monomethyl, diethyl, dimethyl, etc.), acetic acid esters (anisyl, amyl, α-amylcinnamyl, isoamyl, isobutyl, isopropyl, isobornyl, isoeugenyl, eugenyl, 2-ethylbutyl, ethyl, 3-octyl, p-cresyl, o-cresyl, geranyl, α- or β-santalyl, cyclohexyl, cycloneryl, dihydrocuminyl, dimethyl benzyl carbinyl, cinnamyl, styralyl, decyl, dodecyl, terpenyl, guainyl, neryl, nonyl, phenyl ethyl, phenylpropyl, butyl, furfuryl, propyl, hexyl, cis-3-hexenyl, trans-2-hexenyl, cis-3-nonenyl, cis-6-noneyl, cis-3-cis-6-nonadienyl, 3-methyl-2-butenyl, heptyl, benzyl, bornyl, myrcenyl, dihydromyrcenyl, myrtenyl, methyl, 2-methylbutyl, menthyl, linalyl, rhodinyl, etc.), salicylic acid esters (allyl, isoamyl, phenyl, phenylethyl, benzyl, ethyl, methyl, etc.), cyclohexylalkanoic acid esters (ethyl cyclohexylacetate, allyl cyclohexylpropionate, allyl cyclohexylbutyrate, allyl cyclohexylhexanoate, allyl cyclohexyldecanoate, allyl cyclohexylvalerate, etc.), stearic acid esters (ethyl, propyl, butyl, etc.), sebacic acid esters (diethyl, dimethyl, etc.), decanoic acid esters (isoamyl, ethyl, butyl, methyl, etc.), dodecanoic acid esters (isoamyl, ethyl, butyl, etc.), lactic acid esters (menthyl, isoamyl, ethyl, butyl, etc.), nonanoic acid esters (ethyl, phenylethyl, methyl, etc.), nonenoic acid esters (allyl, ethyl, methyl, etc.), hydroxyhexanoic acid esters (ethyl, methyl, etc.), phenylacetic acid esters (isoamyl, isobutyl, ethyl, geranyl, citronellyl, cis-3-hexenyl, methyl, etc.), phenoxyacetic acid esters (allyl, ethyl, methyl, etc.), furancarboxylic acid esters (ethyl furancarboxylate, methyl furancarboxylate, hexyl furancarboxylate, isobutyl furaneopentyl glycol diacetateropionate, etc.), propionic acid esters (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linallyl, terpenyl, α-methylpropionyl, β-methylpropionyl, etc.), heptanoic acid esters (allyl, ethyl, octyl, propyl, methyl, etc.), heptinecarboxylic acid esters (allyl, ethyl, propyl, methyl, etc.), myristic acid esters (isopropyl, ethyl, methyl, etc.), phenylglycidic acid esters (ethyl phenylglycidate, ethyl 3-methylphenylglycidate, ethyl p-methyl-β-phenylglycidate, etc.), 2-methylbutyric acid esters (methyl, ethyl, octyl, phenyl ethyl, butyl, hexyl, benzyl, etc.), 3-methylbutyric acid esters (methyl, ethyl, etc.), butyric acid esters (anisyl, amyl, allyl, isoamyl, methyl, ethyl, propyl, octyl, guainyl, linallyl, geranyl, cyclohexyl, citronellyl, cinnamyl, nellyl, terpenyl, phenylpropyl, β-phenylethyl, butyl, hexyl, cis-3-hexenyl, trans-2-hexenyl, benzyl, rhodinyl, etc.), and hydroxybutyric acid esters (methyl, ethyl, menthyl or the like of 3-hydroxybutyric acid esters).

Examples of alcohols that may be used in fragrance, flavor, and cooling compositions of the present application include, but are not limited to, aliphatic alcohols (isoamyl alcohol, 2-ethylhexanol, 1-octanol, 3-octanol, 1-octene-3-ol, 1-decanol, 1-dodecanol, 2,6-nonadienol, nonanol, 2-nonanol, cis-6-nonenol, trans-2, cis-6-nonadienol, cis-3, cis-6-nonadienol, butanol, hexanol, cis-3-hexenol, trans-2-hexenol, 1-undecanol, heptanol, 2-heptanol, 3-methyl-1-pentanol, etc.); terpene alcohols (borneol, isoborneol, carveol, geraniol, α- or β-santalol, citronellol, 4-thujanol, terpineol, 4-terpineol, nerol, myrcenol, myrtenol, dihydromyrcnol, tetrahydromyrcenol, nerolidol, hydroxycitronellol, farnesol, perilla alcohol, rhodinol, linalool, etc.); and aromatic alcohols (anisic alcohol, α-amylcinnamic alcohol, isopropylbenzylcarbinol, carvacrol, cumin alcohol, dimethylbenzylcarbinol, cinnamic alcohol, phenyl allyl alcohol, phenylethylcarbinol, β-phenylethyl alcohol, 3-phenylpropyl alcohol, benzyl alcohol, etc.).

Examples of carboxamides that may be used in fragrance, flavor, and cooling compositions of the present application include, but are not limited to, acyclic carboxam ides, e.g., N,2,3-trimethyl-2-iso-propyl butanamide, capsaicin, dihydocapsaicin. Other examples of acyclic carboxamides disclosed in US 2005/0265930 are incorporated herein by reference.

Examples of aldehydes that may be used in the fragrance, flavor, and cooling compositions of the present application include, but are not limited to, aliphatic aldehydes (acetaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.); aromatic aldehydes (anisic aldehyde, α-amylcinnamic aldehyde, α-methylcinnamic aldehyde, cyclamen aldehyde, p-isopropylphenylacetaldehyde, ethylvanillin, cumin aldehyde, salicylaldehyde, cinnamic aldehyde, o-, m- or p-tolylaldehyde, vanillin, piperonal, phenylacetaldehyde, heliotropin, benzaldehyde, 4-methyl-2-pheny-2-pentenal, p-methoxycinnamic aldehyde, p-methoxybenzaldehyde, etc.); and terpene aldehydes (geranial, citral, citronellal, α-sinensal, β-sinensal, perillaldehyde, hydroxycitronellal, tetrahydrocitral, myrtenal, cyclocitral, isocyclocitral, citronellyloxyacetaldehyde, neral, α-methylenecitronellal, myracaldehyde, vernaldehyde, safranal, etc.).

Examples of ketones which may be used in the fragrance, flavor, and cooling compositions of the application include, but are not limited to, cyclic ketones (1-acetyl-3,3-dimethyl-1-cyclohexene, cis-jasmone, α-, β- or γ-irone, ethyl maltol, cyclotene, dihydronootkatone, 3,4-dimethyl-1,2-cyclopentadione, sotolon, α-, β-, γ- or δ-damascone, α-, β- or γ-damascenone, nootkatone, 2-sec-butylcyclohexanone, maltol, α-, β- or γ-ionone, α-, β- or γ-methylionone, α-, β- or γ-isomethylionone, furaneol, camphor, etc.); aromatic ketones (acetonaphthone, acetophenone, anisylideneacetone, raspberry ketone, p-methyl acetophenone, anisylacetone, p-methoxy acetophenone, etc.); and chain ketones (diacetyl, 2-nonanone, diacetyl, 2-heptanone, 2,3-heptanedione, 2-pentanone, methyl amyl ketone, methyl nonyl ketone, β-methyl naphthyl ketone, methyl heptanone, 3-heptanone, 4-heptanone, 3-octanone, 2,3-hexanedione, 2-undecanone, dimethyloctenone, 6-methyl-5-hepten-2-one, etc.).

Examples of acetals which may be used in the fragrance, flavor, and cooling compositions of the present application include, but are not limited to, acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenylacetaldehyde dimethyl acetal, citronellyl methyl acetal, acetaldehyde phenylethylpropyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, Ambersage (manufactured by Givaudan), ethyl acetoacetate ethylene glycol acetal, and 2-phenylpropanal dimethyl acetal.

Examples of phenols which may be used in the fragrance, flavor, and cooling compositions of the present application include, but are not limited to, eugenol, isoeugenol, 2-methoxy-4-vinylphenol, thymol, carvacrol, guaiacol, and chavicol, and vanillin.

Examples of ethers which may be used in the fragrance, flavor, and cooling compositions of the present application include, but are not limited to, anethole, 1,4-cineole, dibenzyl ether, linalool oxide, limonene oxide, nerol oxide, rose oxide, methyl isoeugenol, methyl chavicol, isoamyl phenyl ethyl ether, β-naphtyl methyl ether, phenyl propyl ether, p-cresyl methyl ether, vanillyl butyl ether, α-terpinyl methyl ether, citronellyl ethyl ether, geranyl ethyl ether, rosefuran, theaspirane, decylmethyl ether, and methylphenyl methyl ether.

Examples of lactones which may be used in the fragrance, flavor, and/or cooling compositions of the application include, but are not limited to, γ- or δ-decalactone, γ-heptalactone, γ-nonalactone, γ- or δ-hexylactone, γ- or δ-octalactone, γ- or δ-undecalactone, δ-dodecalactone, δ-2-decenolactone, methyl lactone, 5-hydroxy-8-undecenoic acid δ-lactone, jasmine lactone, menthalactone, dihydrocoumarin, octahydrocoumarin, and 6-methylcoumarin.

Examples of furans which may be used in the fragrance, flavor, and cooling compositions of the present application include, but are not limited to, furan, 2-methylfuran, 3-methylfuran, 2-ethylfuran, 2,5-diethyltetrahydrofuran, 3-hydroxy-2-methyltetrahydrofuran, 2-(methoxymethyl)furan, 2,3-dihydrofuran, furfural, 5-methylfurfural, 3-(2-furyl)-2-methyl-2-propenal, 5-(hydroxymethyl)furfural, 2,5-dimethyl-4-hydroxy-3(2H)-furanone (furaneol), 4,5-dimethyl-3-hydroxy-2(5H)-furanone (sotolon), 2-ethyl-4-hydroxy-5-methyl-3(2H)-furanone (homofuraneol), 5-ethyl-3-hydroxy-4-methyl-2(5H)-furanone (homosotolon), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, and furfuryl acetate.

Examples of hydrocarbons which may be used in the fragrance, flavor, and cooling compositions of the present application include, but are not limited to, α- or β-bisabolene, β-caryophyllene, p-cymene, terpinene, terpinolene, cadinene, cedrene, longifolene, farnesene, limonene, ocimene, myrcene, α- or β-pinene, 1,3,5-undecatriene and valencene.

Examples of acids that may be used in the fragrance, flavor, and cooling compositions of the present application include, but are not limited to, geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, and cyclohexanecarboxylic acid.

The fragrance, flavor, and cooling compositions of the application may comprise one or more natural extracts or oils including, but not limited to, anise, orange, lemon, lime, mandarin, petitgrain, bergamot, lemon bairn, grapefruit, elemi, olibanum, lemongrass, neroli, marjoram, *angelica* root, star anise, basil, bay, calamus, chamomile, caraway, cardamom, *cassia*, cinnamon, pepper, *perilla*, cypress, oregano, cascarilla, ginger, parsley, pine needle, sage, hyssop, tea tree, mustard, horseradish, clary sage, clove, cognac, coriander, estragon, *eucalyptus*, fennel, guaiac wood, dill, cajuput, wormseed, pimento, juniper, fenugreek, garlic, laurel, mace, myrrh, nutmeg, spruce, geranium, citronella, lavender, lavandin, palmarosa, rose, rosemary, sandalwood, oakmoss, cedarwood, vetiver, linaloe, bois de rose, patchouli, labdanum, cumin, thyme, ylang ylang, birch, *capsicum*, celery, tolu balsam, genet, immortelle, benzoin, jasmine, cassie, tuberose, *reseda*, marigold, *mimosa*, opoponax, orris, vanilla and licorice. Each of these natural extracts or oils comprises a complex mixture of chemical compounds, which may include those compounds described above. Additional fragrance ingredients may be isolated from natural products, for example, geraniol and citronellal may be isolated from citronella oil, citral may be isolated from lemon-grass oil, eugenol may be isolated from clove oil, and linalool may be isolated from rosewood oil. Animal products used in fragrance compositions include, but are not limited to, musk, ambergris, civet and castoreum. The natural ingredients described herein may also be produced synthetically, and may include the compounds disclosed herein, and be used as fragrance and/or flavor ingredients in the fragrance and flavor compositions of the present application.

Examples of fragrance and cooling ingredients used in perfumes, air fresheners, laundry detergents, pet litters, cleaning products, liquid and bar soaps, shampoos and conditioners, cosmetics, deodorants, and personal hygiene products include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-m ethoxyacetophenone; para-methoxy-alpha-phenylpropene; methyl-2-n-hexyl-3-oxo-cyclopentane carboxylate; undecalactone gamma, geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; and ethylene brassylate.

The fragrance, flavor, and cooling ingredients in a given product's fragrance, flavor, and cooling composition are selected based on the intended use of the product and the product's desired aroma. For example, flavor ingredients used in toothpaste, mouth wash, and dental hygiene products are selected to impart "freshness" and include, but are not limited to, spearmint oil, peppermint oil, star anise oil, lemon oil, and menthol.

Flavor and cooling compositions may be used to mask the unpleasant taste of orally administered medication. For example, if a medication is salty, a flavor composition that has cinnamon, raspberry, orange, maple, butterscotch, or *glycyrrhiza* (licorice) flavor may be used to mask the taste. If the medication is overly sweet, a flavor composition that has a berry, vanilla, or acacia flavor may render the medication more palatable. In the case of bitter tasting medication, flavor compositions that have cocoa, chocolate-mint, wild cherry, walnut, *glycyrrhiza* (licorice), and eriodictyon flavors might be used, whereas sour medications may be improved by flavor compositions that have fruity, citrus, or cherry flavors. These flavors may be provided by the natural or synthetic flavor ingredients discussed herein.

Examples of flavor and cooling ingredients used in flavor and cooling compositions for food products include, but are not limited to, glucosyl steviol glycosides, isomenthols, carbonothoic acids, cassyrane, 1,5-octadien-3-ol, 2-mercaptoheptan-4-ol, 4 3-(methylthio)decanal, (4Z,7Z)-trideca-4,7-dienal, *persicaria odorata* oil, Amacha leaves extract, glutamyl-2-aminobutyric acid, glutamyl-2-aminobutyric acid, glutamyl-norvalyl-glycine, 0 glutamyl-norvaline, N1-(2,3-Dimethoxybenzyl)-N2-(2-(pyridin-2-yl)ethyl) oxalamide, 1-(2-hydroxy-4-methylcyclohexyl)ethanone, Mexican lime oil, Persian lime oil, 6-methoxy-2,6-dimethylheptanal, 3,5-undecadien-2-one, 2,5-undecadien-1-ol, triethylthialdine, 4-methylpentyl 4-methylvalerate, (R)—N-(1-methoxy-4-methylpentan-2-yl)-3,4-dimethylbenzamide, 2 N-acetyl glutamate, 1,3-propanediol, *Szechuan* pepper extract, *Tasmannia lanceolata* extract, *Mentha longifolia* oil, mangosteen distillate, ethyl 3-(2-hydroxyphenyl)propanoate, 1-cyclopropanemethyl-4-methoxybenzene, prenyl thioisobutyrate, prenyl thioisovalerate, matairesinol, stevioside, 1-(2,4-dihydroxyphenyl)-3-(3-hydroxy-4-methoxyphenyl)propan-1-one, Ethyl 5-formyloxydecanoate, 3-[3-(2-isopropyl-5-methyl-cyclohexyl)ureido]butyric acid ethyl ester, 2-Isopropyl-4-methyl-3-thiazoline, 2,6,10-trimethyl-9-undecenal, 5-mercapto-5-methyl-3-hexanone, Meyer lemon oil, teviol glycoside extract, *Stevia rebaudiana*, rebaudioside A 60%, rubescenamine, 4-amino-5-(3-(isopropylamino)-2, 2-dimethyl-3-oxopropoxy)-2-methylquinoline-3-carboxylic acid, 3-methyl-5-(2,2,3-trimethylcyclopent-3-en-1-yl)pent-4-en-2-ol, (1-Methyl-2-(1,2,2-trimethylbicyclo[3.1.0]hex-3-ylmethyl)cyclopropyl)methanol, erospicata oil, and curly mint oil. See L. J. Marnett et al., GRAS Flavoring Substances 26, Food Technology, 44-45 (2013).

Intended uses for fragrance compositions include, but are not limited to, perfumes, air fresheners, laundry detergents, household cleaning solutions, liquid and bar soaps, shampoos and conditioners, hair sprays, cosmetics, deodorants, insect repellants and insecticides, and pet litters.

For example, the fragrance composition of the application may be used in an improved fabric perfume composition (see, e.g., U.S. Pat. No. 6,869,923).

Intended uses for flavor compositions include, but are not limited to, toothpastes, mouthwashes, orally administered medications, and food products.

Intended uses for cooling compositions included, but are not limited to, flavor blends, foods, cosmetic preparations, confectionery, soft and alcoholic beverages, chewing gums, toothpaste, dental floss, mouthwash, anti-plaque, anti-gingivitis compositions, shampoos, antidandruff shampoos, lotions, deodorants, after shave lotions, shaving gels, shaving aid composites, fragrances, skin sanitizing compositions, throat lozenges, throat drops, chewable antacid tablets, or pharmaceutical compositions or medications, including anti-inflammatory compositions, compositions for treatment of nasal symptoms, for upper gastrointestinal tract distress, for treating cold symptoms, for cough relief, for alleviating discomfort of hot flash, or for foot therapy, and the like.

Fragrance, flavor, and cooling compositions of the application may contain a compound of the application in a range of concentrations, e.g., 0.0005% to 99.9% by mass a compound of the application with 99.9995% to 0.1% by mass of one or more additives including, e.g., solvents, surfactants, detergents, and/or other fragrance or flavor components. In one embodiment, a fragrance, flavor, or cooling composition may comprise about 0.0005% to about 10% by mass of a compound of the application with about 99.9995% to about 90% by mass of one or more additives. In one embodiment, a fragrance, flavor, or cooling composition may comprise about 0.0005% to about 1% by mass of a compound of the application with about 99.9995% to about 99% by mass of one or more additives. In one embodiment, a fragrance, flavor, or cooling composition may comprise about 0.05% to about 50% by mass of a compound of the application with about 99.95% to about 50% by mass of one or more additives. In one embodiment, a fragrance, flavor, or cooling composition may comprise about 0.05% to about 10% by mass of a compound of the application with about 99.95% to about 90% by mass of one or more additives. In one embodiment, a fragrance, flavor, or cooling composition may comprise about 0.05% to about 1% by mass of a compound of the application with about 99.95% to about 99% by mass of one or more additives. In one embodiment, a fragrance, flavor, or cooling composition may comprise about 0.5% to about 50% by mass of a compound of the application with about 99.5% to about 50% by mass of one or more additives. In one embodiment, a fragrance, flavor, or cooling composition may comprise about 0.5% to about 10% by mass of a compound of the application with about 99.5% to about 90% by mass of one or more additives. In one embodiment, a fragrance, flavor, or cooling composition may comprise about 0.5% to about 5% by mass of a compound of the application with about 99.5% to about 95% by mass of one or more additives. In one embodiment, a fragrance, flavor, or cooling composition may comprise about 0.5% to about 2.5% by mass of a compound of the application with about 99.5% to about 97.5% by mass of one or more additives. In one embodiment, a fragrance, flavor, or cooling composition may comprise about 2.5% to about 5% by mass of a compound of the application with about 97.5% to about 95% by mass of one or more additives. In one embodiment, a fragrance, flavor, or cooling composition may comprise about 5% to about 7.5% by mass of a compound of the application with about 95% to about 92.5% by mass of one or more additives. In one embodiment, a fragrance, flavor, or cooling composition may comprise about 7.5% to about 10% by mass of a compound of the application with about 92.5% to about 90% by mass of one or more additives. In one embodiment, a fragrance, flavor, or cooling composition may comprise about 10% to about 20% by mass of a compound of the application with about 90% to about 80% by mass of one or more additives. In one embodiment, a fragrance, flavor, or cooling composition may comprise about 20% to about 30% by mass of a compound of the application with about 80% to about 70% by mass of one or more additives. In one embodiment, a fragrance, flavor, or cooling composition may comprise about 30% to about 40% by mass of a compound of the application with about 70% to about 60% by mass of one or more additives. In one embodiment, a fragrance, flavor, or cooling composition may comprise about 40% to about 50% by mass of a compound of the application with about 60% to about 50% by mass of one or more additives. In one embodiment, a fragrance, flavor, or cooling composition may comprise about 50% to about 60% by mass of a compound of the application with about 50% to about 40% by mass of one or more additives. In one embodiment, a fragrance, flavor, or cooling composition may comprise about 60% to about 70% by mass of a compound of the application with about 40% to about 30% by mass of one or more additives. In one embodiment, a fragrance, flavor, or cooling composition may comprise about 70% to about 80% by mass of a compound of the application with about 30% to about 20% by mass of one or more additives. In one embodiment, a fragrance, flavor, or cooling composition may comprise about 80% to about 90% by mass of a compound of the application with about 20% to about 10% by mass of one or more additives. In one embodiment, a fragrance, flavor, or cooling composition may comprise about 85% to about 95% by mass of a compound of the application with about 15% to about 5% by mass of one or more additives. In one embodiment, a fragrance, flavor, or cooling composition may comprise about 90% to about 99.5% by mass of a compound of the application with about 10% to about 0.5% by mass of one or more additives. In one embodiment, a fragrance, flavor, or cooling composition may comprise about 90% to about 98% by mass of a compound of the application with about 10% to about 2% by mass of one or more additives. In one embodiment, a fragrance, flavor, or cooling composition may comprise about 90% to about 95% by mass of a compound of the application with about 10% to about 5% by mass of one or more additives.

In one embodiment, fragrance, flavor, and cooling compositions of the application may contain a compound of the application at 0.005% by mass, 0.01% by mass, 0.02% by mass, 0.03% by mass, 0.04% by mass, 0.05% by mass, 0.06% by mass, 0.07% by mass, 0.08% by mass, 0.09% by mass, 0.1% by mass, 0.2% by mass, 0.3% by mass, 0.4% by mass, 0.5% by mass, 0.6% by mass, 0.7% by mass, 0.8% by mass, 0.9% by mass, 1% by mass, 2% by mass, 3% by mass, 4% by mass, 5% by mass, 6% by mass, 7% by mass, 8% by mass, 9% by mass, 10% by mass, 11% by mass, 12% by mass, 13% by mass, 14% by mass, 15% by mass, 16% by mass, 17% by mass, 18% by mass, 19% by mass, 20% by mass, 21% by mass, 22% by mass, 23% by mass, 24% by mass, 25% by mass, 26% by mass, 27% by mass, 28% by mass, 29% by mass, 30% by mass, 31% by mass, 32% by mass, 33% by mass, 34% by mass, 35% by mass, 36% by mass, 37% by mass, 38% by mass, 39% by mass, 40% by mass, 41% by mass, 42% by mass, 43% by mass, 44% by mass, 45% by mass, 46% by mass, 47% by mass, 48% by mass, 49% by mass, 50% by mass, 51% by mass, 52% by mass, 53% by mass, 54% by mass, 55% by mass, 56% by mass, 57% by mass, 58% by mass, 59% by mass, 60% by mass, 61% by mass, 62% by mass, 63% by mass, 64% by mass, 65% by mass, 66% by mass, 67% by mass, 68% by mass, 69% by mass, 70% by mass, 71% by mass, 72% by mass, 73% by mass, 75% by mass, 76% by mass, 77% by mass, 78% by mass, 79% by mass, 80% by mass, 81% by mass, 82% by mass, 83% by mass, 84% by mass, 85% by mass, 86% by mass, 87% by mass, 88% by mass, 89% by mass, 90% by mass, 91% by mass, 92% by mass, 93% by mass, 94% by mass, 95% by mass, 96% by mass, 97% by mass, 98% by mass, or 99% by mass.

General fragrance and flavor composition additives include, e.g., solvents, excipients, and buffers.

In one aspect, a fragrance composition is provided comprising compound (I), compounds of formula (6), compounds of formula (I'), or compounds of formula (I"). In some embodiments, the fragrance composition may further comprise one or more additives, one or more fragrance ingredients, or a combination thereof.

In one aspect, a product is provided comprising a fragrance composition wherein the fragrance composition comprises compound (I), compounds of formula (6), compounds of formula (I'), or compounds of formula (I"). In one aspect, the product may contain an additional substance, including but not limited to an excipient or a buffer.

In one aspect, a flavor composition is provided comprising compound (I), compounds of formula (6), compounds of formula (I'), or compounds of formula (I"). In one aspect, the flavor composition may further comprise one or more additives, one or more flavor ingredients, or a combination thereof.

In one aspect, a product is provided comprising a flavor composition wherein the flavor composition comprises compound (I), compounds of formula (6), compounds of formula (I'), or compounds of formula (I"). In one aspect, the product may contain an additional substance, including but not limited to an excipient or a buffer.

In one aspect, a cooling composition is provided comprising compound (I), compounds of formula (6), compounds of formula (I'), or compounds of formula (I"). In one aspect, the cooling composition may further comprise one or more additives, one or more cooling ingredients, or a combination thereof.

In one aspect, a product is provided comprising a cooling composition wherein the cooling composition comprises compound (I), compounds of formula (6), compounds of formula (I'), or compounds of formula (I"). In one aspect, the product may contain an additional substance, including but not limited to an excipient or a buffer.

The amount of a given fragrance, flavor, or cooling ingredient in a fragrance, flavor, or cooling composition cannot be categorically described because it varies depending on the type product being scented or flavored, the intended use of the product, and the desired aroma and/or taste of the product. The amount of a fragrance, flavor, or cooling ingredient in a fragrance, flavor, or cooling composition is usually in the range of from about 1% to about 99% by mass of the fragrance, flavor, or cooling composition. When the amount of the ingredient is too small, a sufficient strength of the scent, flavor, or cooling effect may not be obtained. Further, when the amount of the ingredient is too large, a larger amount of the agent(s) needed to solubilize the ingredient may be needed, which may in turn reduce the desired aromatic, flavor, or cooling properties of the end product by inhibiting volatilization or other mechanisms by which the flavor, fragrance, cooling effect is dispersed and/or felt when the product is used or consumed. The amount of each of the fragrance, flavor, or cooling ingredients in a given fragrance, flavor, or cooling composition must therefore be selected based upon the aromatic characteristics, flavor characteristics, and cooling effect of the selected ingredient, the overall composition of the product, and the intended aromatic, flavor, and/or cooling effects.

Additives may be used in the fragrance, flavor, or cooling compositions of the application. Additives that may be used include, but are not limited to, solvents and surfactants. Other fragrance and flavor composition additives will be selected in accordance with the intended use of the composition.

Solvents, for example water-soluble organic solvents, which may be used in the flavor, fragrance, and cooling compositions of the application include, but are not limited to, ethanol, propanol, iso-propanol, butanol, 3-methoxy-3-methyl-1-butanol, benzyl alcohol, ethyl carbitol (diethylene glycol monoethyl ether), ethylene glycol, propylene glycol, dipropylene glycol, butylene glycol, hexylene glycol, glycerin, ethylene glycol monomethyl ether, propylene glycol monomethyl ether, propylene glycol monoethyl ether, and dipropylene glycol monomethyl ether. These water-soluble solvents may be used solely or in combination. The content of the water-soluble organic solvent in the composition may be determined according to the desired composition properties, and is usually from about 1% to about 99% by mass. In one embodiment, the content of the water-soluble solvent is from about 1% to about 10% by mass, from about 5% to about 15% by mass, from about 10% to about 20% by mass, from about 15% to about 25% by mass, from about 20% to about 30% by mass, from about 25% to about 35% by mass, from about 30% to about 40% by mass, from about 35% to about 45% by mass, from about 40% to about 50% by mass, from about 45% to about 55% by mass, from about 50% to about 60% by mass, from about 55% to about 65% by mass, from about 60% to about 70% by mass, from about 75% to about 85% by mass, from about 80% to about 90% by mass, from about 85% to about 95% by mass, from about 90% to about 99% by mass, or from about 95% to about 99% by mass.

In one embodiment, the content of the water-soluble solvent is 99% by mass, 98% by mass, 97% by mass, 96% by mass, 95% by mass, 94% by mass, 93% by mass, 92% by mass, 91% by mass, 90% by mass, 85% by mass, 80% by mass, 75% by mass, 70% by mass, 65% by mass, 60% by mass, 55% by mass, 50% by mass, 45% by mass, 40% by mass, 35% by mass, 30% by mass, 25% by mass, 20% by mass, 15% by mass, 10% by mass, 9% by mass, 8% by mass, 7% by mass, 6% by mass, 5% by mass, 4% by mass, 3% by mass, 2% by mass, or 1% by mass.

Oil-soluble organic solvents which may be used with the flavor, fragrance, and cooling compositions of the application include, but are not limited to, isoparaffin, paraffin, limonene, pinene, triethyl citrate, benzyl benzoate, isopropyl myristate, heptane, triacetin, and silicon.

Preferred solvents include, but are not limited to, triethylcitrate, triacetin, glycerol, heptane, ethyl acetate, ethanol, water, triglycerides, liquid waxes, propylene glycol derivatives, and ethylene glycol derivatives.

The fragrance, flavor, or cooling compositions of the present application may be used in combination with other substances, including, but not limited to, sequestering agents, preservatives, antioxidants, deodorizers, sterilization agents, ultraviolet absorbers, pH adjusters, insecticidal components, components for protection from insects, insect repellents, colorants, excipients, and buffers. The substances used in, or in addition to, the fragrance, flavor, or cooling compositions of the present application may be determined by the product in which the composition is included. When the substance is used in a fragrance, flavor, or cooling composition, it may be an additive. When the substance is used alongside a fragrance, flavor, or cooling composition, it may be considered as part of a product composition that comprises a fragrance, flavor, or cooling composition.

Excipients that may be used in the fragrance, flavor, or cooling compositions of the present application may vary depending on the use of the intended product and its overall composition. In some instances, the excipient may be included in the fragrance, flavor, or cooling composition or may, alternatively, be independent of the composition. Excipients used in or with flavoring or cooling compositions of an orally administered medication include, but are not limited to, tablet coatings, such as a cellulose ether hydroxypropyl methylcellulose, synthetic polymer, shellac, corn protein zein or other polysaccharides, and gelatin. In pet litter, a solid excipient comprised of cellulosic or chlorophyll-containing agents or other materials may be used. In contrast, cosmetic excipients may include, but are not limited to, carbopol 940 ETD, triethanolamine, purified water, glycerine, imidazolidinyl urea, EDTA, 1-polyvinyl alcohol, methyl parabenes phenoxyethanol 0, ethyl alcohol 1, peg 7 glyceryl cocoate, peg 6 triglyceryl caproic glycerides, acemulogar LAM V, isopropylmyristate, tegosoft CT, zantham gum, sepicide CL, polyquaternum 7, and Vaseline oils. Additional suitable excipients for use with or in a fragrance, flavor, or cooling composition for a given product will be readily selected by those having ordinary skill in the art.

Buffers that may be used with the fragrance, flavor, or cooling compositions of the present application may vary depending on the use of the intended product and its overall composition. In some instances, the buffer may be included in the fragrance, flavor, or cooling composition or may, alternatively, be independent of the composition. Examples of buffers that may be used in or with the fragrance, flavor, or cooling compositions of the application include, but are not limited to, citrates, acetates, and phosphates. For example, trisodium citrate may be used as a flavor or as a preservative, and is known to impart tartness to a flavor, but also acts as a buffer. Trisodium citrate is an ingredient in a variety of sodas and other beverages, as well as drink mixes and bratwurst. In cosmetic products, disodium hydrogen phosphate, potassium dihydrogenphosphate, disodium hydrogenphosphate and, and citric acid may be used to buffer the pH of the product. In toothpaste, calcium carbonate and/or dicalcium phosphate may be used as pH buffers. Additional suitable buffers for use with or in a fragrance, flavor, or cooling composition for a given product will be readily selected by those having ordinary skill in the art.

Other fragrance, flavor, and cooling composition additives are selected in accordance with the intended use of the composition.

Examples of fragrance composition additives for use in perfumes include: hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-isopropylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma.

Additional examples of fragrance composition additives for use in perfumes include: geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate.

Examples of cooling composition additives for use in cooling compositions include, but are not limited to, cooling ingredients (e.g., menthyl lactate), solvents (e.g., ethanol or propylene glycol), control release agents or gel-forming agents (e.g., hydroxyalkyl cellulose, starch, or modified starch), and various carriers (e.g., amorphous silica, alumina, or activated carbon).

General Procedure for Preparation of the Compounds of the Application

Starting materials for the aldol condensation reactions can be purchased from a chemical supplier such as Sigma-Aldrich® or can be prepared according to known methods, e.g., oxidation of the corresponding primary or secondary alcohol.

Dienes used in the Diels-Alder reaction are can be purchased from a chemical supplier such as Sigma-Aldrich® or can be prepared according to known methods, e.g., Horner-Wadsworth-Emmons or Wittig olefination reactions.

Diels-Alder reactions are performed as described in the art, but reaction times and conditions may vary depending upon the nature and reactivity of the corresponding diene and alkene. Asymmetric Diels-Alder reactions may be performed as described in the art, see Hayashi, Y. et al. *Angew. Chem. Int. Ed.* 2008, 47, 6634-6637.

Reduction of ketones to the corresponding alcohols are performed as described in the art and often utilize $LiAlH_4$ or di-iso-butyl aluminum hydride. Asymmetric ketone reductions may be performed as described in the art, see Okuma, T. et al. *J. Am. Chem. Soc.* 1995, 117, 10417-10418.

Etherification reactions of cyclohexyl-alkyl carbinols may be accomplished by generating an alkoxide of the corresponding carbinol with a non-nucleophilic base, e.g., potassium tert-butoxide, and reacting with an alkyl iodide or alkyl bromide.

Acylation reactions of cyclohexyl-alkyl carbinols may be accomplished by generating an alkoxide of the corresponding carbinol with a non-nucleophilic base, e.g., potassium tert-butoxide, and reacting with an acid chloride. Alternatively, the carbinol can be reacted with a carboxylic acid using standard esterification reagents and conditions to generate an ester.

Compound (I) may also be prepared as described in Scheme 3, and according to the following synthetic procedure: 3-cyclohexene-1-carboxaldehyde was dissolved into THF and cooled to 0° C. in an ice bath. Iso-propylmagnesium chloride was slowly added over 2 hours. The mixture was then warmed to room temperature and stirred for another hour at room temperature. The reaction was quenched with water, then EtOAc was used to extract the mixture. HOAc (30%) was added to break the gel formed during the extraction. The mixture was brought to pH 8 with $Na_2CO_3$ (10%). The organic phase was then dried with anhydrous $Na_2SO_4$, filtered and evaporated to give crude product: 22 g as a colorless liquid. 8.4 g of product, as a 1:1 mixture of diastereomers was isolated after column chromatography purification.

General Procedure for Odor Detection Thresholds

Odor detection thresholds may be determined using a gas chromatograph. The gas chromatograph is calibrated to allow determination of the exact volume of material injected by the syringe, the precise split ratio, and the hydrocarbon response using a hydrocarbon standard of known concentration and chain-length distribution. The air flow rate is accurately measured, and assuming the duration of a human inhalation to last 12 seconds, the sampled volume is calculated. Since the precise concentration at the detector at any point in time may be determined as described above, the mass per volume inhaled is known, and hence, the concentration of material tested. To determine whether a material has a threshold below 50 ppb, solutions are delivered to the sniff port at a concentration calculated using the method described above. Subsequently, a panelist sniffs the effluent from the gas chromatograph and identifies the retention time at which odor is noticed. Averaged data from all panelists yields the threshold of noticeability.

Definitions

The details of one or more embodiments of the application are set forth in the accompanying description below. Unless defined otherwise, all technical and scientific terms used herein have the same meaning as commonly understood by one of ordinary skill in the art to which this application belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

As used herein, and unless explicitly stated otherwise, the term "about" refers to a recited value +/−10%, +/−5%, +/−2.5%, +/−1%, or +/−0.5%. In one aspect, "about" refers to +/−5%.

As used herein, "$C_1$-$C_6$ alkyl" is intended to include both branched and straight-chain saturated aliphatic hydrocarbon groups having the specified number of carbon atoms. For example, $C_1$-$C_6$ alkyl is intended to include $C_1$, $C_2$, $C_3$, $C_4$, $C_5$, and $C_6$ alkyl groups. Examples of alkyl include, but are not limited to, methyl, ethyl, n-propyl, iso-propyl, n-butyl, s-butyl, t-butyl, n-pentyl, s-pentyl, and n-hexyl. "$C_1$-$C_6$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

$C_3$-$C_6$ cycloalkyl refers to any of cyclopropyl, cyclobutyl, cyclopentyl or cyclohexyl.

$C_4$-$C_6$ dicarboxylic acid refers to compounds with 4, 5, or 6 carbon atoms and two carboxylic acid moieties. Examples include, without limitation, succinic acid, glutaric acid, adipic acid, maleic acid, fumaric acid, glutaconic acid, muconic acid, glutinic acid, citraconic acid, and mesaconic acid.

"Enantiomeric excess" or "ee" refers to a measure for how much of one enantiomer is present compared to the other. For a mixture of R and S enantiomers, the percent enantiomeric excess is defined as |R−S|*100, where R and S are the respective mole fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

"Enantioenriched" refers to a non-racemic mixture of enantiomers, i.e., a mixture in which one enantiomer is present in higher amounts than the other enantiomer.

"Diastereoenriched" refers to a mixture of stereoisomers in which one diastereomer is present in higher amounts than the other diastereomers in the mixture.

It is to be noted that "cosmetic products" mean products to keep the personal appearance clean or fine; specific examples thereof include soaps, body-cleansing agents, hair-cleansing agents, hair cosmetics, cosmetics (for example, skin cosmetics and finish cosmetics), perfumes, colognes, antiperspirants, deodorants and bath agents.

It is to be noted that "household products" mean products to maintain the functionality and cleanliness of various articles necessary for domestic life such as houses themselves and household articles; specific examples thereof include clothes detergents, clothes softeners, clothes starch, house detergents, bath detergents, dish detergents, bleaching agents, mildew cleaners and floor waxes.

It is to be noted that "environmental/sanitary products" mean products to regulate the environment at predetermined conditions or atmospheres, in particular, products capable of regulating, by applying fragrance compositions, an odor floating in the environment; specific examples of such products include air fresheners, deodorants, incense fragrances, incense sticks and candles.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

EXAMPLES

Example 1: Odor Detection

Odor detection thresholds may be determined using a gas chromatograph. The gas chromatograph is calibrated to allow determination of the exact volume of material injected by the syringe, the precise split ratio, and the hydrocarbon response using a hydrocarbon standard of known concentration and chain-length distribution. The air flow rate is accurately measured, and assuming the duration of a human inhalation to last 12 seconds, the sampled volume is calculated. Since the precise concentration at the detector at any point in time may be determined as described above, the mass per volume inhaled is known, and hence, the concentration of material tested. To determine whether a material has a threshold below 50 ppb, solutions are delivered to the sniff port at a concentration calculated using the method described above. Subsequently, a panelist sniffs the effluent from the gas chromatograph and identifies the retention time at which odor is noticed. Averaged data from all panelists yields the threshold of noticeability.

A calculated amount of analyte is injected onto the gas chromatograph column to achieve a 50 ppb concentration at the detector. Typical gas chromatograph parameters for determining odor detection thresholds via the method described above are listed below.

GC: 5890 Series II with FID detector
7673 Autosampler
Column: J&W Scientific DB-1
Length 30 meters ID 0.25 mm film thickness 1 micron
Method:
Split Injection: 17/1 split ratio
Autosampler: 1.13 microliters per injection
Column Flow: 1.10 mL/minute
Air Flow: 345 mL/minute
Inlet Temp. 245° C.
Detector Temp. 285° C.
Temperature Information
Initial Temperature: 50° C.
Rate: 5 C/minute
Final Temperature: 280° C.
Final Time: 6 minutes
Leading assumptions:
  (i) 12 seconds per sniff
  (ii) GC air adds to sample dilution Example 2: Synthesis of compound (I), 1-(cyclohex-3-en-1-yl)-2-methylpropan-1-ol 3-cyclohexene-1-carboxaldehyde (16.5 g, 0.15 mol) was dissolved into THF (300 mL) and cooled to 0° C. in an ice bath. Iso-propyl magnesium chloride (3M in THF, 92.5 mL) was slowly added over 2 hours. The mixture was then warmed to room temperature and stirred for another hour at room temperature. The reaction was quenched with water (100 mL), then EtOAc (500 mL) was used to extract the mixture. HOAc (30%) was added to break the gel formed during the extraction. The mixture was brought to pH 8 with $Na_2CO_3$ (10%). The organic phase was then dried with anhydrous $Na_2SO_4$, filtered and evaporated to give crude product: 22 g as a colorless liquid. 8.4 g of product, as a 1:1 mixture of diastereomers was isolated after column chromatography purification (silica gel, EtOAc/heptane as eluent).

$^1$H NMR ($CDCl_3$, 400 MHz) δ 0.89-0.97 (m, 6H, —$CH_3$), 1.21-1.47 (m, 1H, —CH—), 1.62-1.85 (m, 2H, —$CH_2$—), 1.90-2.13 (m, 4H, —$CH_2$—, OH), 3.12-3.18 (m, 1H, —CHOH), 5.66-5.71 (m, 2H, —CH═CH—).

Example 3: Olfactory Analysis of Compound (I)

When compound (I) is presented on the fragrance blotter neat, it has a minty aroma that can be described as fresh, invigorating, and menthol-like.

The entire disclosure of each of the patent documents and scientific articles referred to herein is incorporated by reference for all purposes.

The application can be embodied in other specific forms without departing from the spirit or essential characteristics thereof. The foregoing embodiments are therefore to be considered in all respects illustrative rather than limiting on the application described herein. Scope of the application is thus indicated by the appended claims rather than by the foregoing description, and all changes that come within the meaning and range of equivalency of the claims are intended to be embraced therein.

What is claimed:

1. A perfume, soap, air freshener, laundry detergent, household cleaning product, liquid or bar soap, shampoo, conditioner, hairspray, cosmetic, makeup, deodorant, insect repellant, insecticide, or pet litter, comprising a fragrance composition comprising 1-(cyclohex-3-en-1-yl)-2-methylpropane-1-ol (compound (I)); or a mouth wash, toothpaste, floss, breath freshener, orally administered liquid, tablet or capsule medication, or food product, comprising a flavor composition comprising 1-(cyclohex-3-en-1-yl)-2-methylpropane-1-ol (compound (I)); or a flavor blend, food, cosmetic preparation, confectionery, soft beverage, alcoholic beverage, chewing gum, toothpaste, dental floss, mouthwash, anti-plaque composition, anti-gingivitis composition, shampoo, lotion, deodorant, after shave lotion, shaving gel, shaving aid composition, fragrance, skin sanitizing composition, throat lozenge, throat drop, chewable antacid tablet, pharmaceutical composition or medication, comprising a physiologically cooling composition comprising 1-(cyclohex-3-en-1-yl)-2-methylpropane-1-ol (compound (I)).

2. The composition according to claim 1, comprising one or more additives, one or more fragrance agents or flavor agents or cooling agents, or a combination thereof.

3. The composition according to claim 2, wherein the one or more additives is a surfactant.

4. The composition according to claim 2, wherein the one or more additives is an oil.

5. The composition according to claim 1, wherein the concentration of compound (I) is 0.0005% to 99.9% by mass, 0.05% to 50% by mass, or 0.5% to 10% by mass.

6. The composition of claim 1, wherein stereoisomer Ia, is present in compound (I) in an amount greater than about 50%, or in an amount greater than about 90%.

7. The composition of claim 1, wherein stereoisomer Ib, is present in compound (I) in an amount greater than about 50%, or in an amount greater than about 90%.

8. The composition of claim 1, wherein stereoisomer Ic,

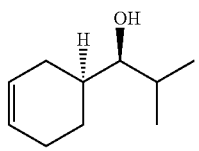

is present in compound (I) in an amount greater than about 50%, or in an amount greater than about 90%.

9. The composition of claim 1, wherein stereoisomer Id,

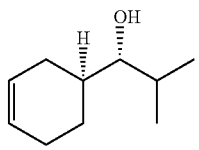

is present in compound (I) in an amount greater than about 50%, or in an amount greater than about 90%.

10. The composition of claim 1, wherein the composition is a perfume, soap, air freshener, laundry detergent, household cleaning product, liquid or bar soap, shampoo, conditioner, hairspray, cosmetic, makeup, deodorant, insect repellant, insecticide, or pet litter.

11. The composition of claim 1, wherein the composition is a mouth wash, toothpaste, floss, breath freshener, orally administered liquid, tablet or capsule medication, or food product.

12. The composition of claim 1, wherein the composition is a flavor blend, food, cosmetic preparation, confectionery, soft beverage, alcoholic beverage, chewing gum, toothpaste, dental floss, mouthwash, anti-plaque composition, anti-gingivitis composition, shampoo, lotion, deodorant, after shave lotion, shaving gel, shaving aid composition, fragrance, skin sanitizing composition, throat lozenge, throat drop, chewable antacid tablet, pharmaceutical composition or medication.

* * * * *